(12) United States Patent  (10) Patent No.: US 8,518,692 B2
Wilson  (45) Date of Patent: Aug. 27, 2013

(54) GAS PERMEABLE CELL CULTURE DEVICE AND METHOD OF USE

(75) Inventor: John R. Wilson, New Brighton, MN (US)

(73) Assignee: Wilson Wolf Manufacturing Corporation, New Brighton, MN (US)

( * ) Notice: Subject to any disclaimer, the term of this patent is extended or adjusted under 35 U.S.C. 154(b) by 726 days.

(21) Appl. No.: 12/499,633

(22) Filed: Jul. 8, 2009

(65) Prior Publication Data

US 2010/0055774 A1  Mar. 4, 2010

Related U.S. Application Data

(60) Provisional application No. 61/078,966, filed on Jul. 8, 2008.

(51) Int. Cl.
*C12M 1/12* (2006.01)
(52) U.S. Cl.
USPC .................. 435/297.5; 435/297.1; 435/289.1
(58) Field of Classification Search
USPC .......... 435/287.1, 289.1, 297.1, 297.5, 304.2, 435/401
See application file for complete search history.

(56) References Cited

U.S. PATENT DOCUMENTS

| | | | |
|---|---|---|---|
| 3,459,176 A | 8/1969 | Leonard | |
| 3,839,155 A | 10/1974 | McAleer et al. | |
| 3,853,712 A | 12/1974 | House et al. | |
| 3,870,602 A | 3/1975 | Froman et al. | |
| 3,873,423 A | 3/1975 | Munder et al. | |
| 3,941,661 A | 3/1976 | Noteboom | |
| 4,228,243 A | 10/1980 | Iizuka | |
| 4,296,205 A | 10/1981 | Verma | |
| 4,317,886 A | 3/1982 | Johnson et al. | |
| 4,435,508 A | 3/1984 | Gabridge | |
| 4,654,308 A | 3/1987 | Safi et al. | |
| 4,661,455 A | 4/1987 | Hubbard | |
| 4,668,632 A | 5/1987 | Young et al. | |
| 4,717,668 A | 1/1988 | Keilman et al. | |
| 4,734,373 A | 3/1988 | Bartal | |

(Continued)

FOREIGN PATENT DOCUMENTS

| CA | 2105419 | 3/1994 |
|---|---|---|
| DE | 4229334 | 3/1994 |

(Continued)

OTHER PUBLICATIONS

File History for U.S. Publication No. 2005/0106717, published May 19, 2005.

(Continued)

*Primary Examiner* — Michael Hobbs
(74) *Attorney, Agent, or Firm* — Patterson Thuente Pedersen, P.A.

(57) ABSTRACT

Gas permeable devices and methods are disclosed that provide highly efficient cell culture. Gas compartments, made up at least in part of gas permeable material, are dispersed within the culture device in locations that allow cells to remain within a fixed distance from a gas transmission location as the device scales in the horizontal direction. Gas permeable walls of the gas compartment(s) allow gas exchange with the ambient gas. Such an arrangement provides many advantages including the ability to eliminate the need for a gas-liquid interface, allow cell culture to proceed in the static mode (i.e. absent the need for media or gas to be pumped through the device), allow the scale of the device to increase in both the horizontal direction and vertical direction, reduce the rate of media evaporation, allow uncomplicated and low cost device fabrication, and provide the capacity for reduced feeding frequency.

22 Claims, 19 Drawing Sheets

(56) References Cited

U.S. PATENT DOCUMENTS

| | | |
|---|---|---|
| 4,748,124 A | 5/1988 | Vogler |
| 4,824,787 A | 4/1989 | Serkes et al. |
| 4,829,002 A | 5/1989 | Pattillo et al. |
| 4,829,004 A | 5/1989 | Varani et al. |
| 4,839,292 A | 6/1989 | Cremonese |
| 4,847,462 A | 7/1989 | Soodak et al. |
| 4,906,577 A | 3/1990 | Armstrong et al. |
| 4,912,058 A | 3/1990 | Mussi et al. |
| 4,937,194 A | 6/1990 | Pattillo et al. |
| 4,937,196 A | 6/1990 | Wrasidlo et al. |
| 4,939,151 A | 7/1990 | Bacehowski et al. |
| 4,945,203 A | 7/1990 | Soodak et al. |
| 4,960,706 A | 10/1990 | Bliem et al. |
| 5,026,650 A | 6/1991 | Schwarz et al. |
| 5,047,347 A | 9/1991 | Cline |
| 5,068,195 A | 11/1991 | Howell et al. |
| 5,078,755 A | 1/1992 | Tozawa et al. |
| 5,139,951 A | 8/1992 | Butz et al. |
| 5,153,131 A | 10/1992 | Wolf et al. |
| 5,173,225 A | 12/1992 | Range et al. |
| 5,225,346 A | 7/1993 | Matsumiya et al. |
| 5,240,854 A | 8/1993 | Berry et al. |
| 5,310,676 A | 5/1994 | Johansson et al. |
| 5,324,428 A | 6/1994 | Flaherty |
| 5,330,908 A | 7/1994 | Spaulding |
| 5,426,037 A | 6/1995 | Pannell et al. |
| 5,437,998 A | 8/1995 | Schwarz et al. |
| 5,449,617 A | 9/1995 | Falkenberg et al. |
| 5,503,741 A | 4/1996 | Clark |
| 5,527,705 A | 6/1996 | Mussi et al. |
| 5,576,211 A | 11/1996 | Falkenberg et al. |
| 5,578,492 A | 11/1996 | Fedun |
| 5,650,325 A | 7/1997 | Spielmann |
| 5,659,997 A | 8/1997 | Sprehe et al. |
| 5,670,332 A | 9/1997 | Kuhl et al. |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,702,945 A | 12/1997 | Nagels et al. |
| 5,707,869 A | 1/1998 | Wolf et al. |
| 5,714,384 A | 2/1998 | Wilson et al. |
| 5,783,075 A | 7/1998 | Eddleman et al. |
| 5,866,400 A | 2/1999 | Palsson et al. |
| 5,866,419 A | 2/1999 | Meder |
| 5,902,747 A | 5/1999 | Nemser et al. |
| 5,914,154 A | 6/1999 | Nemser |
| 5,924,583 A | 7/1999 | Stevens et al. |
| 5,928,936 A | 7/1999 | Ingram |
| 5,935,847 A | 8/1999 | Smith et al. |
| 5,963,537 A | 10/1999 | Fujisawa |
| 5,985,653 A | 11/1999 | Armstrong et al. |
| 5,989,913 A | 11/1999 | Anderson et al. |
| 6,063,618 A | 5/2000 | Weuster-Botz et al. |
| 6,130,080 A | 10/2000 | Fuller |
| 6,150,159 A | 11/2000 | Fry |
| 6,190,913 B1 | 2/2001 | Singh |
| 6,228,607 B1 | 5/2001 | Kersten et al. |
| 6,297,046 B1 | 10/2001 | Smith et al. |
| 6,306,491 B1 | 10/2001 | Kram et al. |
| 6,455,310 B1 | 9/2002 | Barbera-Guillem |
| 6,468,792 B1 | 10/2002 | Bader |
| 6,562,616 B1 | 5/2003 | Toner et al. |
| 6,569,675 B2 | 5/2003 | Wall et al. |
| 6,605,463 B1 | 8/2003 | Bader |
| 6,759,245 B1 | 7/2004 | Toner et al. |
| 6,855,542 B2 | 2/2005 | DiMilla et al. |
| 6,900,055 B1 | 5/2005 | Fuller et al. |
| 7,229,820 B2 | 6/2007 | Wilson |
| 7,560,274 B1 | 7/2009 | Fuller et al. |
| 2003/0008388 A1 | 1/2003 | Barbera-Guillem et al. |
| 2003/0017142 A1 | 1/2003 | Toner et al. |
| 2003/0077816 A1 | 4/2003 | Kronenthal et al. |
| 2003/0143727 A1 | 7/2003 | Chang |
| 2003/0157709 A1 | 8/2003 | DiMilla et al. |
| 2003/0203477 A1 | 10/2003 | Hyman et al. |
| 2004/0029266 A1 | 2/2004 | Barbera-Guillem |
| 2004/0043481 A1 | 3/2004 | Wilson |
| 2004/0067585 A1 | 4/2004 | Wang et al. |
| 2004/0072347 A1 | 4/2004 | Schuler et al. |
| 2004/0110199 A1 | 6/2004 | Montemagno et al. |
| 2005/0032205 A1 | 2/2005 | Smith et al. |
| 2005/0089993 A1 | 4/2005 | Boccazzi et al. |
| 2005/0106717 A1 | 5/2005 | Wilson et al. |
| 2005/0148068 A1 | 7/2005 | Lacey et al. |
| 2007/0026516 A1 | 2/2007 | Martin et al. |
| 2007/0254356 A1 | 11/2007 | Wilson |
| 2008/0176318 A1 | 7/2008 | Wilson |
| 2008/0206857 A1 | 8/2008 | Kenney et al. |
| 2008/0227176 A1 | 9/2008 | Wilson |
| 2009/0160975 A1 | 6/2009 | Kwan |
| 2010/0255576 A1 | 10/2010 | Wilson |
| 2011/0129923 A1 | 6/2011 | Wilson |
| 2011/0287542 A1 | 11/2011 | Wilson |
| 2011/0287543 A1 | 11/2011 | Wilson |

FOREIGN PATENT DOCUMENTS

| | | |
|---|---|---|
| EP | 0 155 237 A2 | 9/1985 |
| EP | 264464 | 4/1988 |
| EP | 353893 | 2/1990 |
| EP | 0647707 | 4/1995 |
| EP | 0 700 900 | 3/1996 |
| EP | 0 866 122 A2 | 9/1998 |
| EP | 0 890 636 B1 | 10/2001 |
| EP | 1245670 | 10/2002 |
| FR | 2 666 094 | 2/1992 |
| GB | 2268187 | 1/1994 |
| JP | 59220182 | 12/1984 |
| JP | 62 032875 | 2/1987 |
| JP | 6434283 | 7/1987 |
| JP | 5-123182 | 5/1993 |
| JP | 78267 | 1/1995 |
| JP | 11-028083 | 2/1999 |
| JP | 2002-528567 | 9/2002 |
| JP | 2002-335946 | 11/2002 |
| JP | 2002335946 | 11/2002 |
| JP | 2003503022 | 1/2003 |
| JP | 2006217845 | 8/2006 |
| JP | 2008048653 | 3/2008 |
| WO | WO9600780 | 1/1996 |
| WO | WO 9630497 | 10/1996 |
| WO | WO98/17362 | 4/1998 |
| WO | WO9853894 | 12/1998 |
| WO | WO 00/23331 | 4/2000 |
| WO | WO 00/24437 | 5/2000 |
| WO | WO 00/56870 | 9/2000 |
| WO | WO00/58437 | 10/2000 |
| WO | WO0078920 | 12/2000 |
| WO | WO0078932 | 12/2000 |
| WO | WO 01/92462 A1 | 12/2001 |
| WO | WO 02064730 | 8/2002 |
| WO | WO03/060061 | 7/2003 |
| WO | WO03064990 | 8/2003 |
| WO | WO2005035728 | 4/2005 |
| WO | WO 2008/073314 A2 | 6/2008 |
| WO | WO 2010006055 A2 | 1/2010 |

OTHER PUBLICATIONS

File History for U.S. Publication No. 2008/0227176, published Sep. 18, 2008.
Giarratana et al., Cell culture bags allow a large extent of ex vivo expansion of LTC-IC and functional mature cells which can subsequently be frozen: interest for large-scale clinical applications. Bone Marrow Transplantation, Oct. 1998, vol. 22, No. 7, pp. 707-715.
CLINIcell® 250 commercial product and related User Instructions V-2, date unknown.
LifeCell® X-Fold™ Culture Bag commercial product and related literature, © 2000.
Opticell® commercial product and related literature, © 2000.
OriGen PermaLife™ commercial product and related literature, at least as of Sep. 17, 2004.
VectraCell™ commercial product and related literature, at least as of Sep. 18, 2004.

VueLife™ Culture Bag commercial product and related literature, at least as of Oct. 28, 2003.

petriPERM commercial product and related literature, © 2003.

English Translation of Japanese Office Action (Notice of Reasons for Rejection) for Japanese Application No. 2006-534398 dated Nov. 9, 2010.

Written Opinion from International Application No. PCT/US2009/049944 dated Jan. 20, 2011.

Nagel et al., Membrane-based cell culture systems—an alternative to in vivo production of monoclonal antibodies. Dev Biol Stand, 1999, vol. 101, pp. 57-64.

Secker et al., Gas-permeable lifecell tissue culture flasks give improved growth of *Helicobacter pylori* in a liquid medium., J Clin Microbial, May 1991, vol. 29, No. 5, pp. 1060-1061.

Canadian Office Action for Canadian Application No. 2,671,812 dated Feb. 28, 2011.

Canadian Office Action for Canadian Application No. 2,671,967 dated Mar. 1, 2011.

Machine Translation of JP-05123182 dated May 12, 1993.

Examiner's first report on Australian Patent Application No. 2011200410 dated Aug. 30, 2011.

Papas et al, "High-Density Culture of Human Islets on Top of Silicone Rubber Membranes" Transplantation Proceedings, vol. 37 (2005) pp. 3412-3414.

File Wrapper for EP Publication No. 1687400 published Aug. 9, 2006. 225 pages.

Publication re: VueLife™ Culture bags distributed by CellGeniz, known to applicant at least as early as Sep. 17, 2004. 4 pages.

Genetic Engineering News "OptiCell Concept for Cell Culture Operations". vol. 20, No. 21. Dec. 2000. 4 pages.

Japanese Final Decision of Rejection dated Aug. 2, 2011 for Japanese Application No. 2006-534398.

Canadian Office Action for Canadian Application No. 2,542,116 dated Aug. 30, 2011.

Application and File History for U.S. Appl. No. 13/194,298, filed Jul. 29, 2011, inventor Wilson.

Application and File History for U.S. Appl. No. 13/194,363, filed Jul. 29, 2011, inventor Wilson.

Machine Translation of JP78267 dated Jan. 13, 1995.

Machine Translation of JP6434283 dated Jul. 29, 1987.

European Search Report for European Application No. 11158157.5 dated Dec. 15, 2011.

Chinese Office Action from Chinese Application No. 200780051037.5 dated Sep. 26, 2011.

Budhiono et al., "Kinetic Aspects of Bacterial Cellulose Formation in nata-de-coco Culture System", Carbohydrate Polymers. vol. 40. pp. 137-143 (1999).

Pulvertaft et al, "Activiation of Lymphocytes" J. Clin. Path . vol. 20 pp. 795-805 (1967).

Text of the 2nd Office Action from Chinese Application No. 2004800326848 dated Jan. 21, 2012.

Application and File History for U.S. Appl. No. 13/029,762, filed Feb. 17, 2011 inventors Wilson et al.

Machine Translation of Japanese Referencoe JPH07-034699.

Babblefish Translation of FR 2666094.

Mathiot et al, "Increase of hybridoma productivity using an original dialysis culture system." Cytotechnology, vol. 11 (1993) pp. 41-48.

Jensen Mona D., et al., "Diffusion in Tissue Cultures on Gas-permeable and Impermeable Supports", J. Theor,. Biol. 56, 443-458 (1976).

Jensen, Mona D., "Mass cell culture in a controlled environment", Cell Culture and its Applications, Academic Press (1977).

Jensen, Mona D., "Production of Anchorage-Dependent Cells—Problems and their Possible Solutions," Biotechnology and Bioengineering, vol. XXIII, pp. 2703-2716 (1981).

Techno Plastics. Web Catalog. Jan 2003. http://web.archive.org/web/20031209110901/http://www/tpp.ch/tis.

Vogler, E. A., "A Compartmentalized Device for the Culture of Animal Cells", Biomat., Art. Cells, Art. Org., 17(5), 597-610 (1989).

International Search Report for International Application No. PCT/US07/25110 dated May 20, 2008.

International Search Report for International Application No. PCT/US07/25108 dated May 28, 2008.

Written Opinion of the International Searching Authority for International Application No. PCT/US2007/025108 dated May 28, 2008.

Japanese Office Action for Japanese Application No. 2006-534398 date May 25, 2010.

Chinese Office Action for Chinese Application No. 200480032684.8 dated Jul. 1, 2010.

Written Opinion of the International Searching Authority for International Application No. PCT/US07/25110 dated May 20, 2008.

Application and File History for US Publication No. 2005/0106717, published May 19, 2005, inventor Wilson.

Application and File History for US Publication No. 2008/0227176, published Sep. 18, 2008, inventor Wilson.

Application and File History for US Publication No. 2007/0254356 published Nov. 1, 2007, inventor Wilson.

Application and File History for US Publication No. 2010/025576 filed Oct. 7, 2010, inventor Wilson.

Application and File History for US Publication No. 2008/0176318 published Jul. 24, 2008, inventor Wilson.

US 6,465,252, 10/2002, Toner et al. (withdrawn)

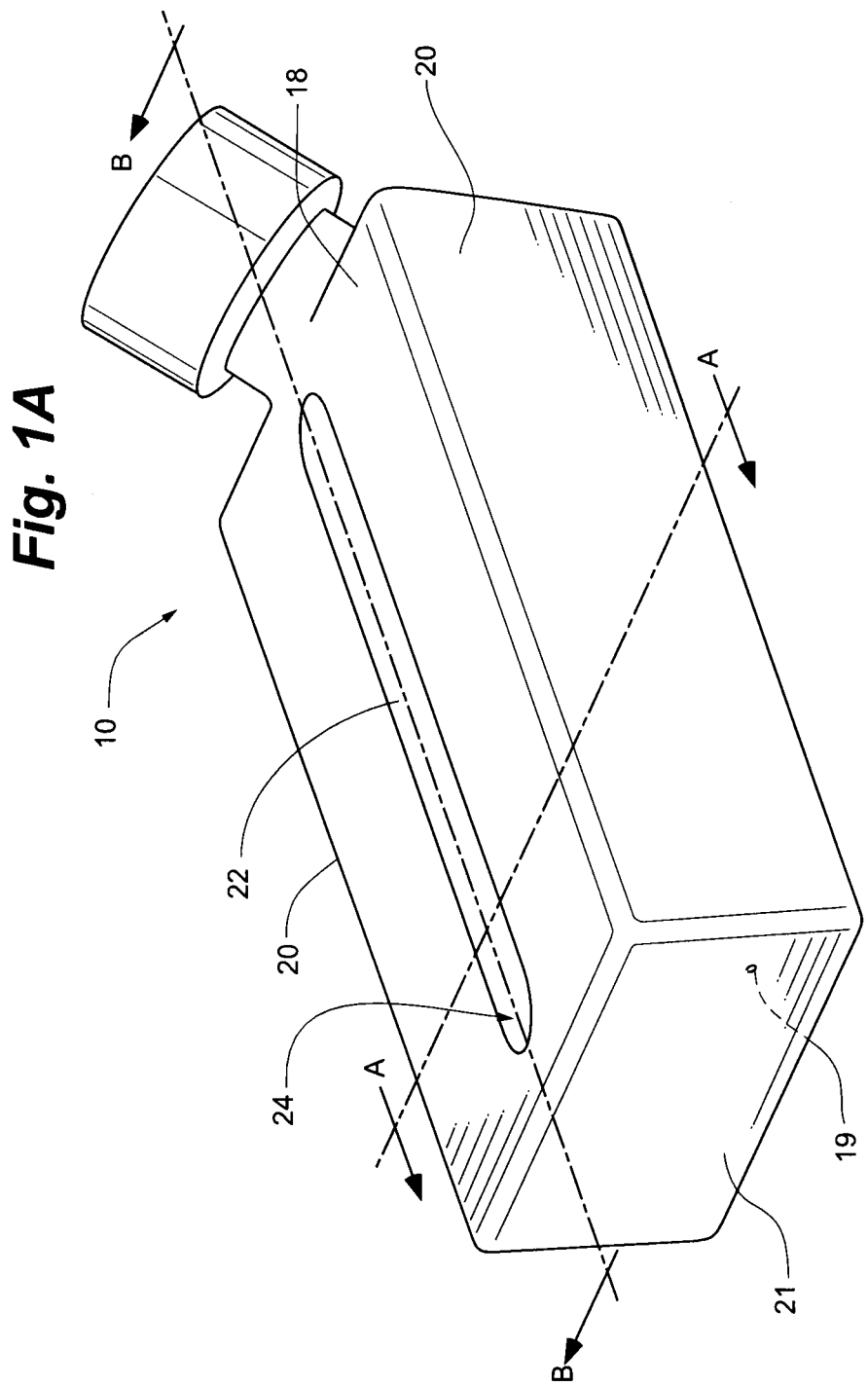

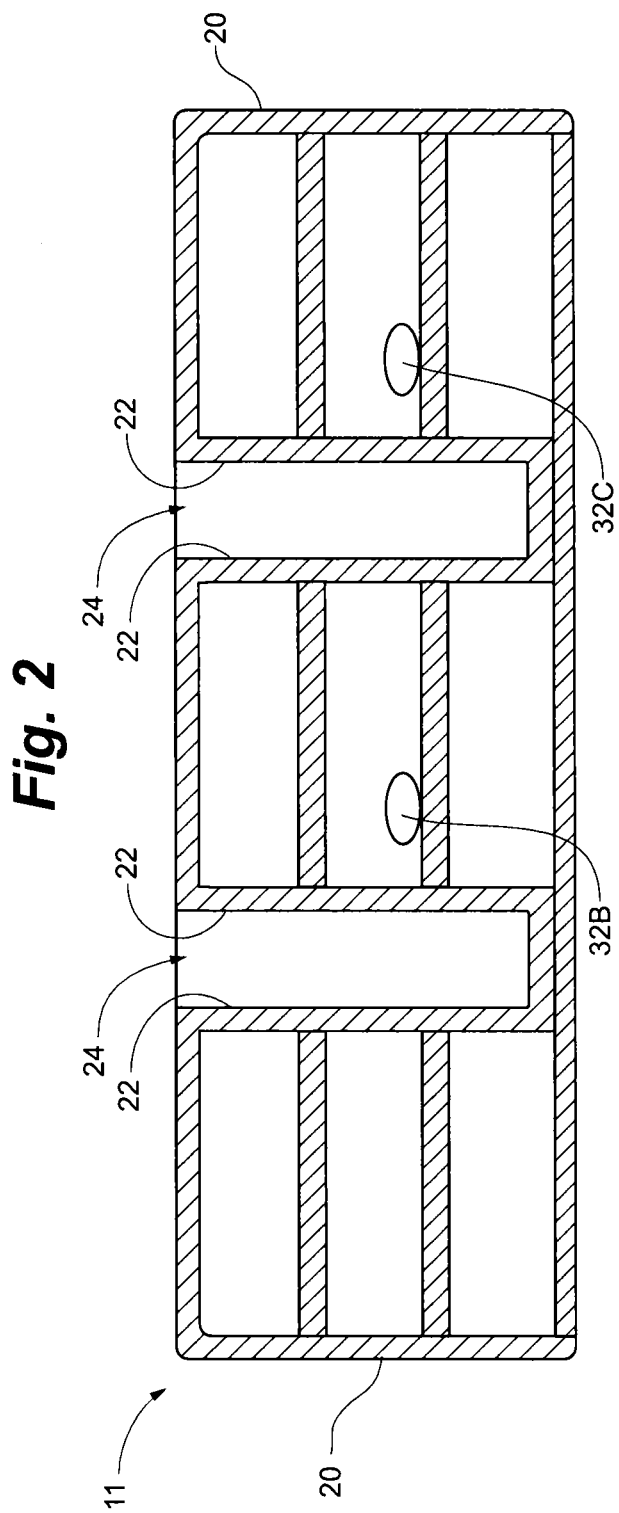

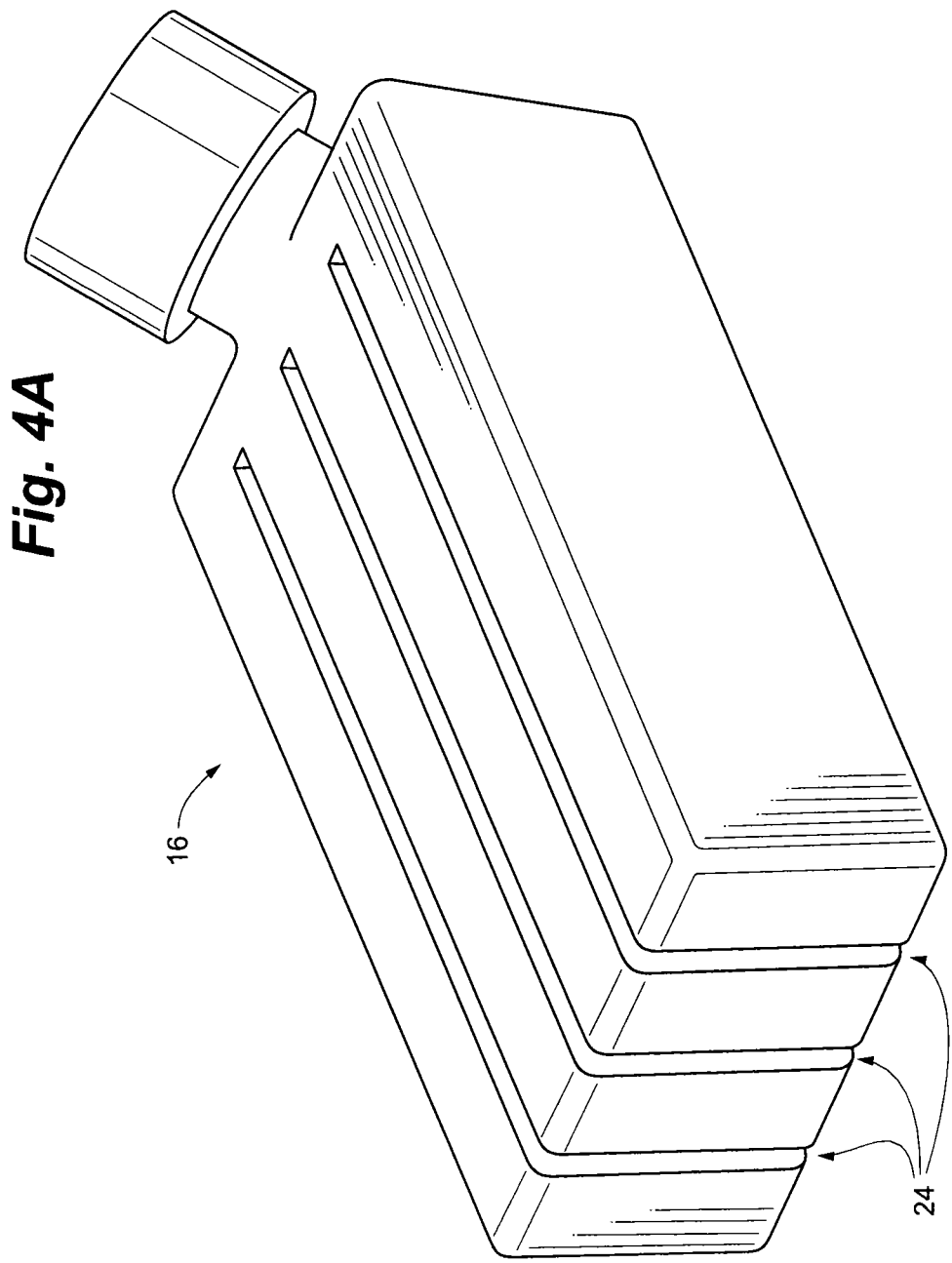

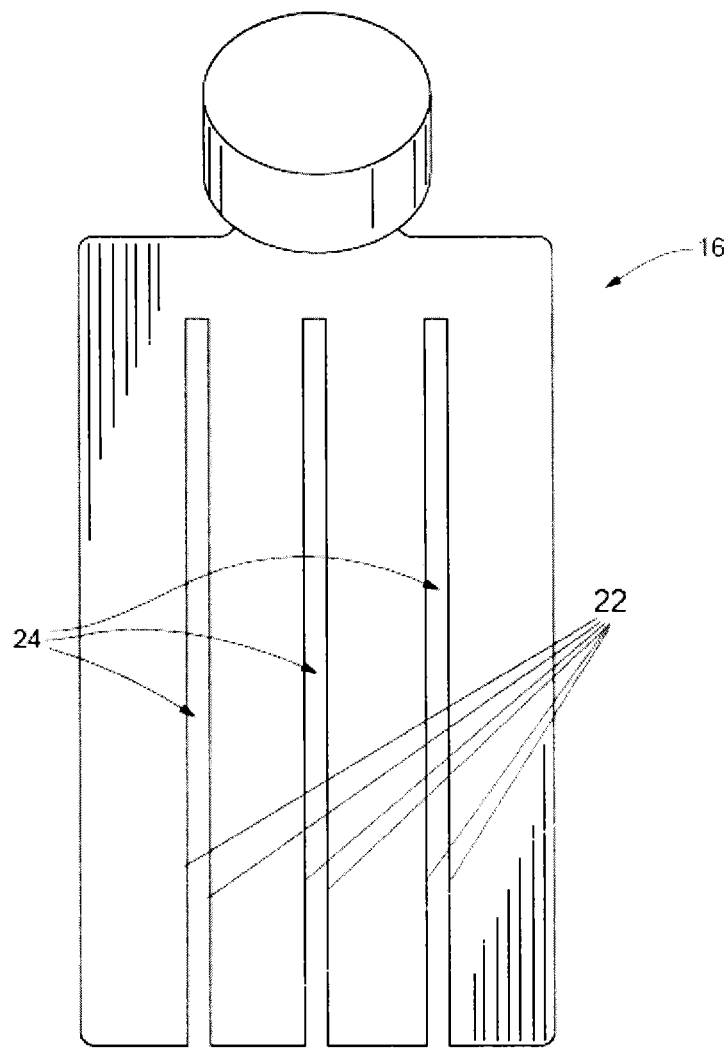

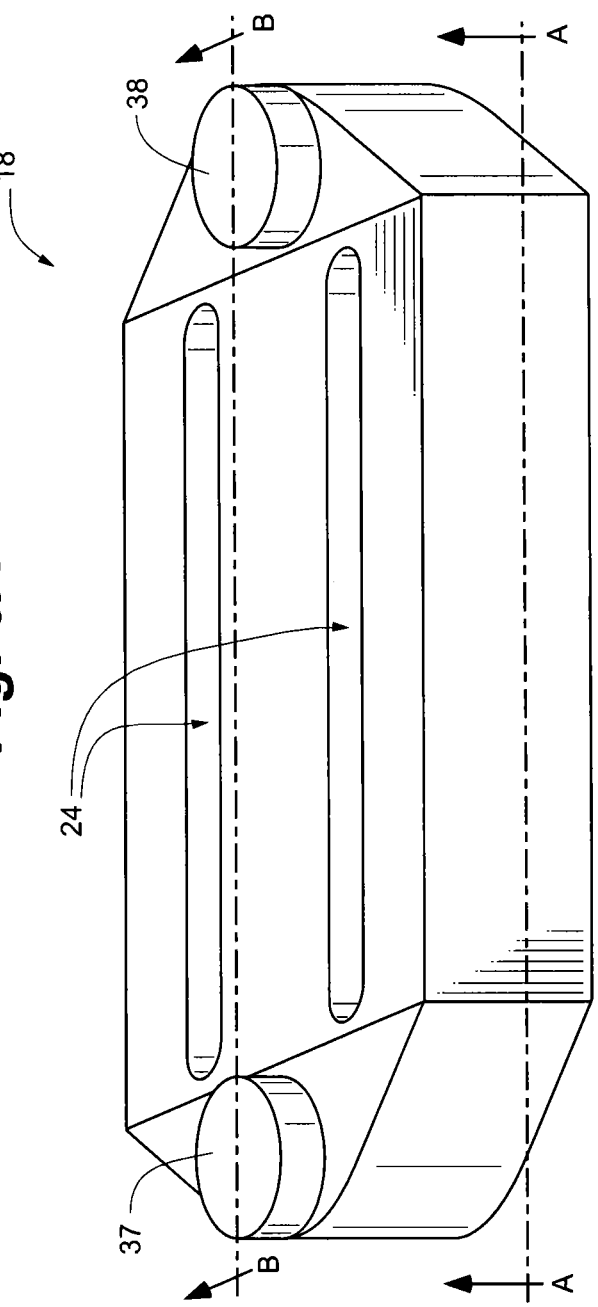

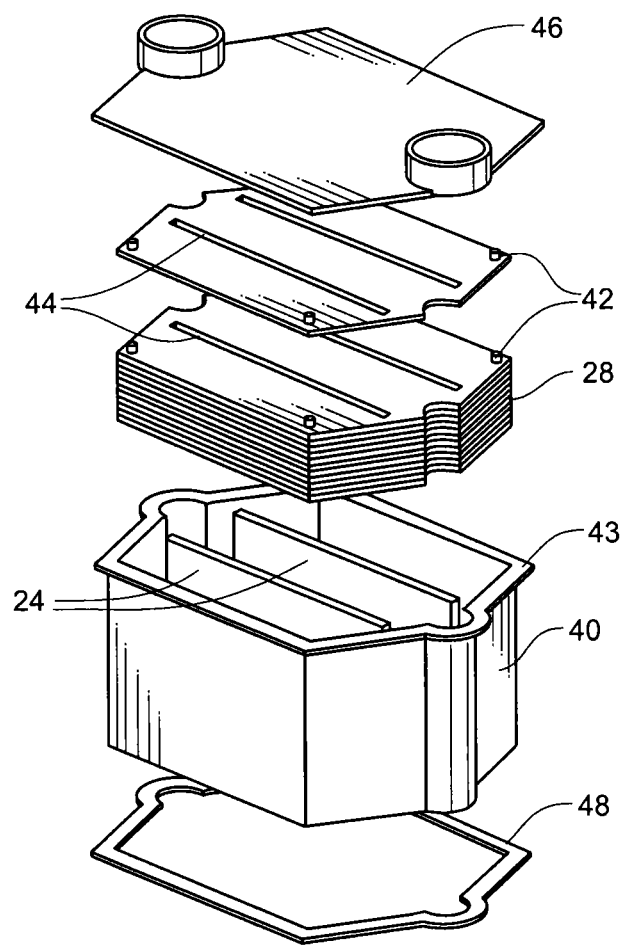

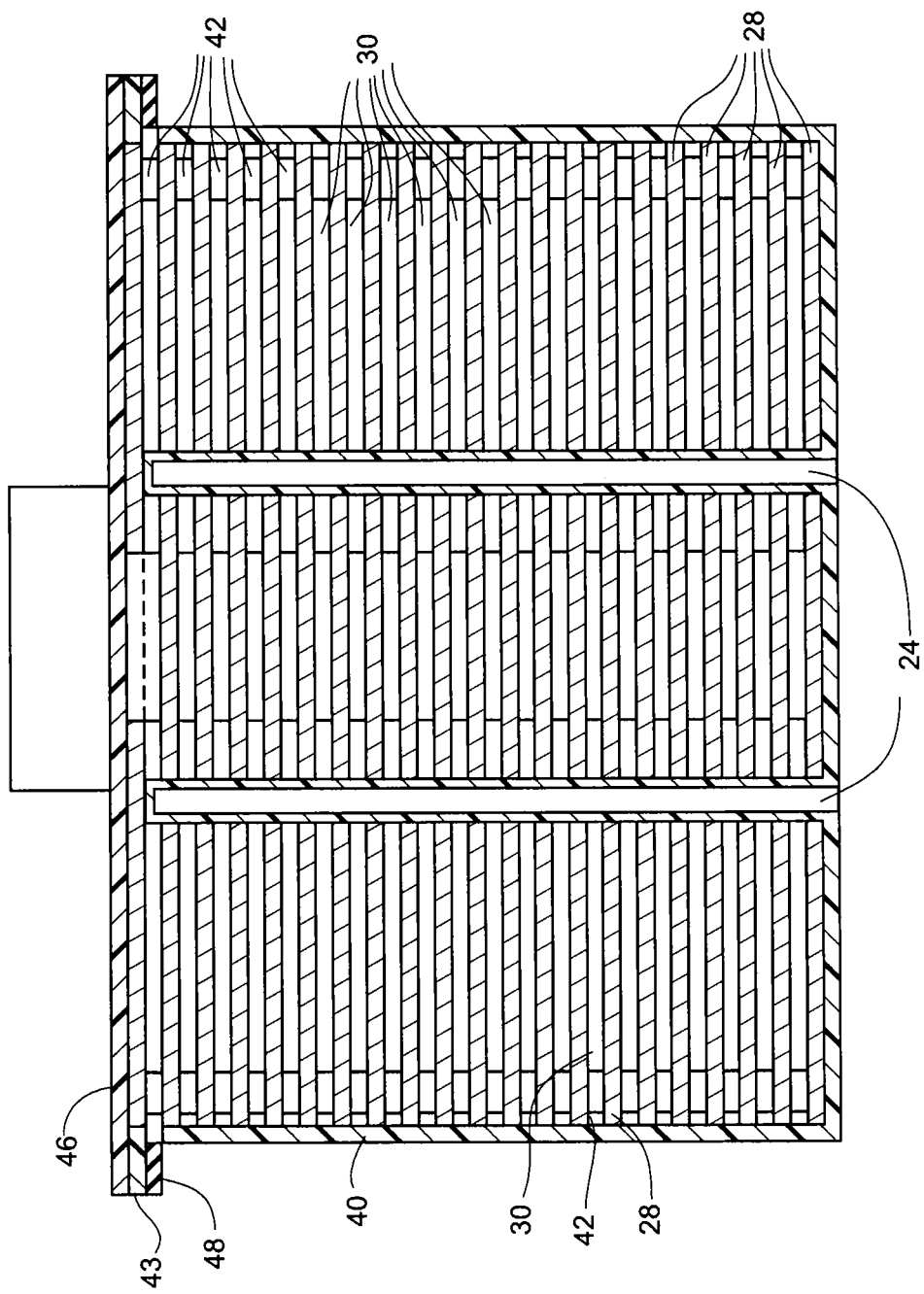

GAS PERMEABLE CELL CULTURE DEVICE AND METHOD OF USE

RELATED APPLICATION

This application claims the benefit of U.S. Provisional Application No. 61/078,966, filed Jul. 8, 2008, which is hereby fully incorporated herein by reference.

GOVERNMENT INTERESTS

This invention was made in part with U.S. Government support under National Institutes of Health Small Business Innovative Research Grant R43 GM077778-01 entitled "Highly efficient gas permeable cell culture devices."

TECHNICAL FIELD

The technical field of this invention is related to gas permeable cell culture devices and cell culture methods that allow a more efficient cell culture process.

BACKGROUND OF THE INVENTION

Each of the applications, patents, and papers cited in this application and in co-pending U.S. application Ser. No. 10/961,814, U.S. application Ser. No. 11/952,848, U.S. application Ser. No. 11/952,856 as well as each document or reference cited in each of the applications, including during the prosecution of each co-pending patent application and each of the PCT and foreign applications or patents corresponding to and/or claiming priority from any of these applications and patents, and each of the documents cited or referenced in each of the application cited documents, are hereby expressly incorporated herein.

For scale up of adherent cell culture, multiple shelf flasks such as the Nunc Cell Factory and Corning® Cell Stack are commonly used. However, to provide oxygen to the cells during culture, these devices require each shelf to have gas reside above the medium. This need for gas to be present in the device makes the device large and awkward to handle during scale up, wasting laboratory space and requiring the use of special equipment during media exchange. The net result is a complicated and costly process as cultures increase in size. The need for a gas-liquid interface to oxygenate the culture is the root cause of these inefficiencies.

Co-pending U.S. patent application Ser. No. 10/961,814 (Wilson et al.) describes multiple shelf devices that eliminates the need for gas to reside above each shelf. In one embodiment, a series of shelf-like scaffolds for cells to reside upon are arranged one above the other and at least a portion of the outer wall(s) of the device is gas permeable. The gas permeable outer wall(s) is oriented perpendicular to the scaffolds. Gas transmission through the gas permeable outer walls(s) allows cells to be oxygenated in the absence of a gas-liquid interface. The culture can proceed without need to perfuse media or gas (i.e. operates in a static mode), allowing a simple cell production method. However, as the device gets wider, the distance a cell can get from the oxygen source increases. At some point, a cell can get too far from the oxygen source and the device scalability in the horizontal direction becomes limited. Thus, although the device is more compact than traditional devices, its scalability in the horizontal direction is limited.

Co-pending U.S. patent application Ser. No. 11/952,848 (Wilson) also describes devices that eliminate the need for gas to reside above each shelf. In various embodiments, a series of cell compartments are arranged one above the other. The bottom of each cell compartment is gas permeable. In use, cells can reside upon the gas permeable surfaces, which act to function as gas permeable scaffolds. This allows each cell to be a uniform distance from the ambient oxygen source as the devices scales horizontally and vertically. However, this type of device can be more difficult and expensive to manufacture than the devices described in co-pending '814, elevating its cost to the end user. Furthermore, since more gas permeable surface area is present, evaporation of media in the device can occur at a higher rate than the traditional multiple shelf flask and the devices of co-pending '814. Configurations are disclosed that minimize this problem, but they add features that increase cost.

Although co-pending '848 and co-pending '814 provide a more space efficient geometry than traditional multiple shelf flasks, there are cell culture applications for which neither co-pending '848 nor co-pending '814 are ideal. As just one example, stem cells are often cultured at low surface density so that cells do not get too close to each other in order to prevent unwanted differentiation. As the number of cells that the culture is intended to generate increases, the culture device needs to provide a larger amount of surface area to keep the cells at low surface density. Therefore, a device that allows scale up in the vertical and horizontal direction is useful. To make the most efficient use of space, it should function in the absence a gas-liquid interface and not require equipment to pump media or gas through it. Although co-pending '848 provides those attributes, the extra cost to place cells a uniform distance from ambient gas is not warranted since few cells are present for each square centimeter of area that cells reside upon (i.e. low oxygen demand). The lower cost devices of co-pending '814 have limited scalability in the horizontal direction. Thus, a new device configuration is needed that is inexpensive to manufacture, easy to use, eliminates the need for a gas-liquid interface, does not require perfusion, and fills the void between co-pending '848 and co-pending '814. Such a device would cost reduce and simplify the cell manufacturing process for many important cell culture applications such as stem cell culture.

Accordingly, an improved gas permeable device is disclosed that is easy to manufacture, can function in the absence of a gas-liquid interface, does not require equipment to pump media or gas through it, and allows virtually unlimited scalability in the horizontal and vertical direction.

SUMMARY OF THE INVENTION

The invention described herein allows highly efficient cell culture. Gas compartments, comprised at least in part of gas permeable material, are dispersed within the culture device in locations that allow cells to remain within a fixed distance from a gas transmission location as the device scales in the horizontal direction. Gas permeable walls of the gas compartment(s) allow gas exchange with the ambient gas. Such an arrangement provides many advantages including the ability to eliminate the need for a gas-liquid interface, allow cell culture to proceed in the static mode (i.e. absent the need for media or gas to be pumped through the device), allow the scale of the device to increase in both the horizontal direction and vertical direction, reduce the rate of media evaporation, allow uncomplicated and low cost device fabrication, and provide the capacity for reduced feeding frequency.

In one embodiment, a gas permeable cell culture device include scaffolds arranged one above the other with a space separating them to form cell compartments. A manifold connects an access port to the cell compartments. At least one gas permeable gas compartment is in contact with the cell compartments, thereby enhancing gas transmission between cell compartments and ambient gas.

In another embodiment, the gas compartment includes walls that are oriented perpendicular to the scaffolds.

In another embodiment, the gas compartment opening to ambient gas is located on the bottom of the gas permeable device.

In another embodiment, the gas compartment opening to ambient gas is located on the top of the device.

In another embodiment, the gas compartment opening to ambient gas is located on the side wall of the device.

In another embodiment, the gas compartment opening to ambient gas is located on the top and/or bottom and side wall of the device.

In another embodiment, the gas compartment opening to ambient gas is traverses the entire gas permeable device with a gas opening on opposing walls of the gas permeable device.

In another embodiment, the gas compartment includes a gas compartment support structure.

BRIEF DESCRIPTION OF THE DRAWINGS

FIG. 1A is a perspective view of an illustrative embodiment of the present invention. The contents of gas permeable device 10 are in communication with ambient gas by a gas permeable exterior walls and gas compartment 24.

FIG. 2 is a cross-sectional view of an illustrative embodiment of the present invention showing how the distance between cells and walls that provide gas transmission can be altered by the number and location of gas compartments.

FIG. 4A is a perspective view of an illustrative embodiment of the present invention showing how the gas compartment(s) can be part of the device perimeter.

FIG. 4B is a top view of an illustrative embodiment of the present invention showing how the gas compartment(s) can be part of the device perimeter.

FIG. 6A shows a perspective view of an illustrative embodiment of the present invention configured to allow cells and medium to enter the device with minimal turbulence.

FIG. 7A is an exploded view of an illustrative embodiment of the present invention showing how a preferred embodiment can be assembled.

FIG. 7C is a cross-sectional view of the illustrative embodiment shown in FIG. 7A in an assembled state.

DETAILED DESCRIPTION OF THE DRAWINGS

Figure 1B:
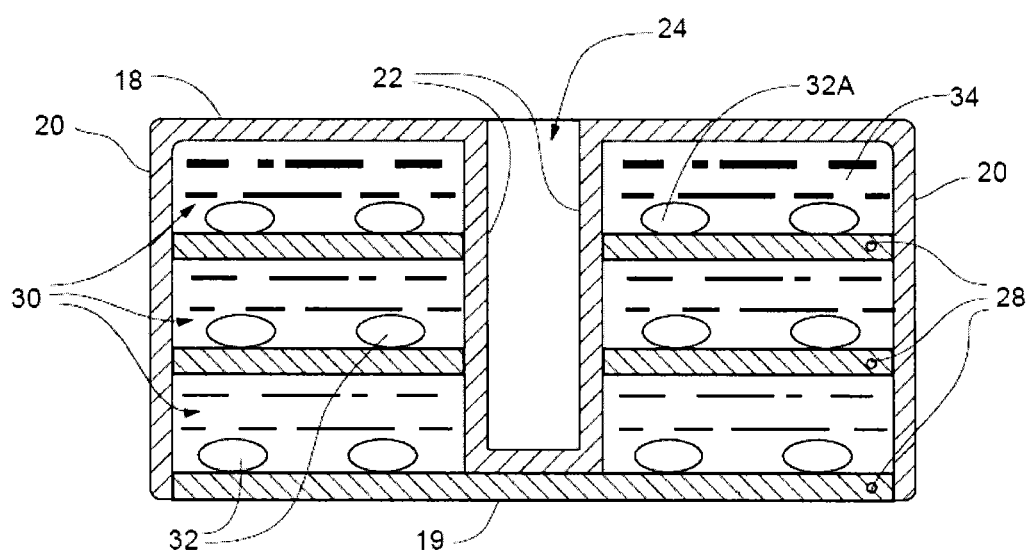
FIG. 1B is cross-sectional view A-A of the device of FIG. 1A, exhibiting how use of gas compartment 24 reduces the distance between cells and the gas compartment walls.

FIG. 1A shows a perspective view of one embodiment of the present invention. The exterior of gas permeable device 10 includes top 18, side walls 20, rear side wall 21, and bottom 19. Gas compartment 24 descends from top 18 into gas permeable device 10. Gas compartment 24 is structured to allow ambient gas to be in contact with its wall(s) 22. Selected walls 22 and/or areas of walls 22 are gas permeable. In this embodiment, one opening to gas compartment 24 is present and is located at top 18. Allowing gas transmission through selected portions of gas compartment 24 allows improved gas exchange between the contents of gas permeable device 10 and ambient gas. In this manner, the device can reside in a standard $CO_2$ incubator while gas compartment 24 facilitates gas exchange of the culture residing within the gas permeable device. In addition to the gas compartment, the exterior walls of the gas permeable device can be gas permeable, further enhancing gas transfer.

FIG. 1B shows a cross-sectional view A-A of the device of FIG. 1A when in use and helps explain the advantage of gas compartment 24. In this depiction, cells 32 and cell culture medium 34 are shown in the device. Cells 32 have settled upon scaffolds 28. Scaffolds 28 reside one above the other, with the space between scaffolds 28 forming cell compartments 30. Cell compartments 30 are thus bounded on the upper and lower sides by scaffolds 28, except the most elevated cell compartment 30 which is bounded on the lower side by scaffold 28 and on the upper side by top 18. Preferably, gas compartment 24 occupies a portion of each cell compartment 30. Unlike a traditional multiple shelf flask, gas need not be present in cell compartments 30 for gas permeable device 10 to function. In this depiction, medium 34 fills cell compartments 30. Preferably, the distance between each scaffold 28 (i.e. the height of the cell compartment) should be equal and scaffolds 28 should be parallel to each other for uniform cell distribution and culture conditions. Since the typical recommended medium height in traditional flask culture is between 2 mm and 3 mm, making the distance between scaffolds 2 mm to 3 mm will lead to similar feeding frequency as traditional flasks. Increasing the distance between scaffolds can be undertaken in order to decrease feeding frequency, since doing so will increase the medium volume to scaffold surface area ratio and provide more solutes for each square centimeter of growth area. Stated differently, more medium in each cell compartment relative to the medium above each shelf of a traditional flask can reduce feeding frequency.

Figure 1C:
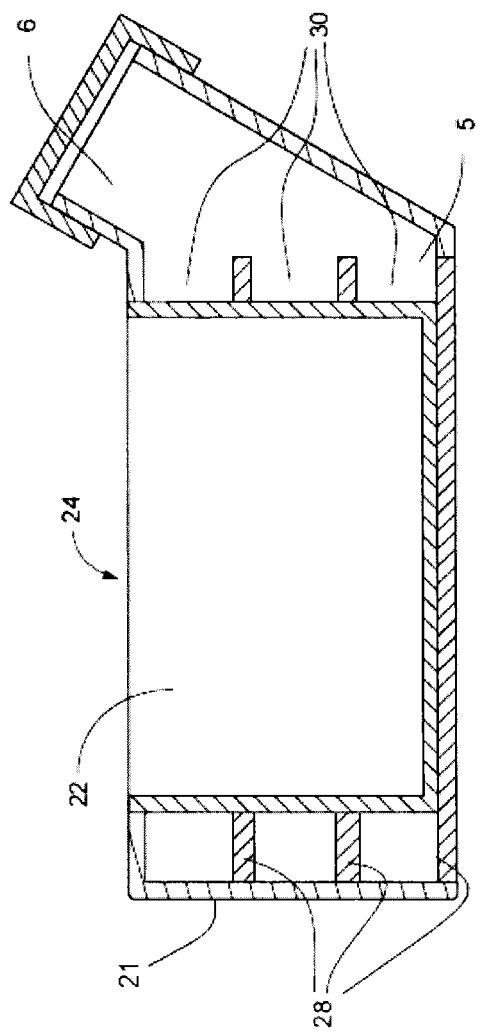
FIG. 1C is cross-sectional view B-B of the device of FIG. 1A, exhibiting design considerations for inoculation and media exchange.

FIG. 1C shows cross-sectional view B-B of FIG. 1A. Gas compartment 24 extends along the length of scaffolds 28 and penetrates cell compartments 30. Manifold 5 resides between scaffolds 28 and access port 6, allowing media to be added and removed from cell compartments 30 via access port 6. Manifold 5 acts to channel medium into each cell compartment 30. Preferably, gas compartment 24 extends the greatest practical distance along the length of scaffolds 28 in order to maximize the uniformity of the conditions within gas permeable device 10 as they relate to gas exchange. The amount of surface area of gas compartment wall 22 that is gas permeable depends on fabrication methods and the amount of gas transmission needed for a given cell culture application. Maximizing the surface area that is gas permeable can increase the gas transmission into each cell compartment 30. Preferably, gas transmission capacity provided by gas compartment 24 is uniformly distributed to each cell compartment 30. In short, the gas compartments are preferably structured to create an equal capacity for gas transfer from cell compartment to cell compartment. Even if the entire surface of the gas compartments is gas permeable, the evaporative effect is less than the embodiments of '848. Thus, another advantage is the ability to increase the size of the device in the horizontal direction relative to embodiments of '814 while reducing the evaporative effects relative to embodiments of '848.

Controlling the area where cells can deposit during inoculation is a design consideration. When the device is filled with inoculum, each cell gravitates to the area of the device directly below it. Preferably the design allows at least 90%, and more preferably 95%, of cells to gravitate to scaffolds in a uniform pattern of distribution. Thus, manifold 5 should occupy the smallest volume of space possible while still facilitating easy delivery and removal of media. Scaffolds 28 may or may not make liquid tight contact with side wall(s) 20 and rear side wall 21. A gap between scaffolds 28 and adjacent walls may exist if it is easier to fabricate the device in that manner or if it is determined that a greater cross-section for movement of solutes from cell compartment to cell compartment is needed than can be provided by the manifold(s). If it is determined that a gap will exist, be aware that cells gravitating from inoculum will fall through the gap to the lowest scaffold (or bottom) and seed at a surface density that is higher than other areas of the scaffolds. Note that the same physical relationship between the scaffolds and the exterior walls holds for the scaffolds and the gas compartment walls. Thus, the gap includes the distance between scaffolds and adjacent walls. The gap area and manifold area contribute to the quantity of cells that do not seed uniformly on scaffolds. In a preferred embodiment, the distance between scaffolds and exterior walls, except at the manifold location, is about 0.2 inch or less.

The presence of gas compartment 24 acts to reduce the distance a cell resides from a gas transmission location. To help explain this concept and referring again to FIG. 1B, consider side walls 20 and gas compartment walls 22 as gas permeable. The presence of gas compartment 24 allows cell 32A to reside at a shorter distance to an area of the device where gas transmission occurs than it would in the absence of gas compartment 24.

The purpose of the gas compartment(s) is to allow ambient gas (typically incubator gas) to reside within the gas compartment(s) of the novel device. The movement of ambient gas is driven by a concentration difference that develops during culture between the contents of the cell compartments and the ambient gas. For example, during culture a concentration gradient forms across the gas permeable material causing gas (such as oxygen and carbon dioxide) to be transmitted from the side of the gas permeable material that exhibits the highest concentration to the side that exhibits the lowest. For example, typically a gradient of oxygen forms such that oxygen is transmitted from a standard cell culture incubator into the cell compartments of the novel device.

Gas compartments are most preferably structured to allow ambient gas to freely enter gas compartments, absent forced flow by ancillary apparatus such as pumps. By so structuring the gas compartments, inlet and outlet ports for directing forced gas flow are not needed. Gas moves rapidly during convection and the distance between the closest opposing walls of the gas compartment need only be great enough such that gas can move at a greater rate than the culture demands it. In general, the greater the depth of the gas compartment from the outer surface of the device, the wider the gas compartment should be. Too narrow a cross-section could restrict air flow. Making the width small generally serves the purpose of making the device more compact in size. However, the space savings already provided by eliminating the need for a gas-liquid interface are substantial. Thus, a cross-sectional width of the opening to the gas compartment is about 0.1 inches or greater is preferred. Also, the shape of the opening preferably remains constant throughout the depth of the gas compartment. For example, for a rectangular opening with a width of 0.1 inch, the gas compartment walls would remain generally parallel and at a distance of about 0.1 inch throughout the gas compartment. Since the volume of space displaced by the gas compartments is relatively small in comparison to the volume of the gas permeable device, greater distances do not cause much lost space. Thus, depending on the width and height of the device, and the number of gas compartments employed, a cross-sectional width of the opening to the gas compartment of up to 1 inch could effectively allow gas transmission without much impact on the footprint of the device.

There are many possible options for the geometry and the material that comprise the gas compartments. The length, width, depth, gas transmission rate, and all other aspects of the gas compartment can be altered to meet the needs of a given cell culture application. Gas permeable materials that are liquid impermeable are preferred, such as dimethyl silicone. However, co-pending '856 describes how liquid permeable materials can be used.

The location and number of gas compartments can be altered to control the distance at which cells can reside from a gas transmission location. As the gas permeable device scales to a larger size in the horizontal direction, more and more gas compartments can be added. FIG. 2 shows a cross-sectional view of a gas permeable device 11, modified to reduce the maximum distance at which cells, such as cell 32B and cell 32C, can reside from a gas transmission area. In this depiction, two gas compartments 24 descend into gas permeable device 11. In the case where side walls 20 and gas compartment walls 22 are gas permeable, it can be seen how gas compartments 24 allow cells 32B and 32C to be closer to gas transmission areas than they would in the absence of gas compartments 24. Thus, the ability to maintain acceptable oxygen tension in the culture media as the device scales horizontally is achieved by the use of gas compartments and gas permeable walls that allow cells to be in proximity of ambient gas.

Gas compartments need not descend into cell compartments to allow cells to be closer to gas compartment walls. Any arrangement that diminishes the distance at which a cell resides from a gas permeable wall(s) can exist. For example, gas compartments can ascend into, traverse through, and/or move completely through the gas permeable cell culture device. Examples are shown in FIG. 3A, FIG. 3B, FIG. 3C, and FIG. 3D, where gas compartments 24, gas permeable wall(s) 22 of gas compartments 24, device side walls 20, scaffolds 28, and/or cell compartments 30 can be seen in relation to each other. In all cases, any exterior walls of the gas permeable device can be gas permeable as an option, but at least a portion of the gas compartment must be gas permeable. How to determine when to rely on gas permeable exterior device walls, such as side walls, will be described herein.

Figure 3A:
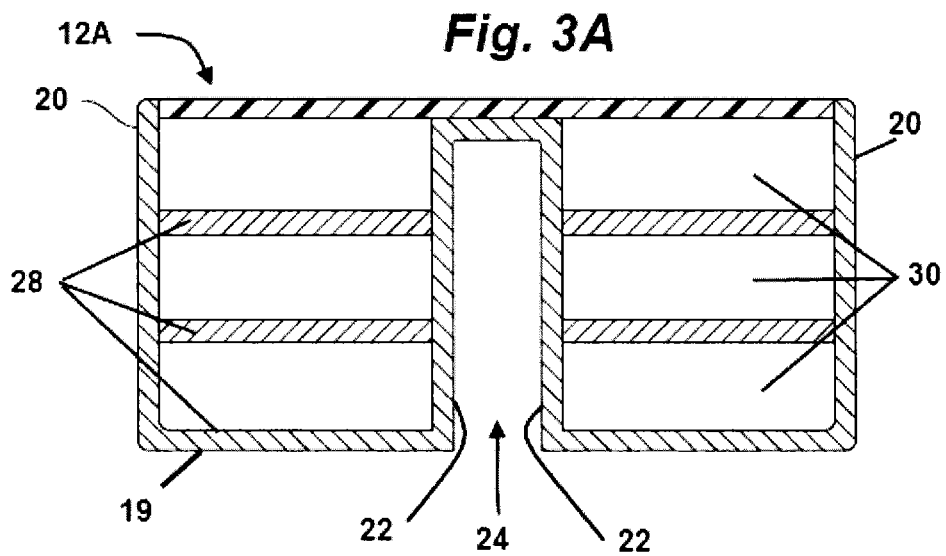
FIG. 3A is a cross-sectional view of an illustrative embodiment of the present invention showing how the gas compartment(s) can ascend into the gas permeable cell culture device.

FIG. 3A shows cross-sectional view of an illustrative embodiment of the present invention. Gas permeable cell culture device 12A includes a gas compartment 24 that ascends into gas permeable cell culture device 12A. One opening to gas compartment 24 is present and is located at bottom 19. Walls 22 of gas compartment 24, comprised of gas permeable material, provide gas transmission to cell compartments 30. Cell compartments 30 are bounded on their lower side by scaffolds 28. Gas compartment 24 is present in each cell compartment 30.

Figure 3B:
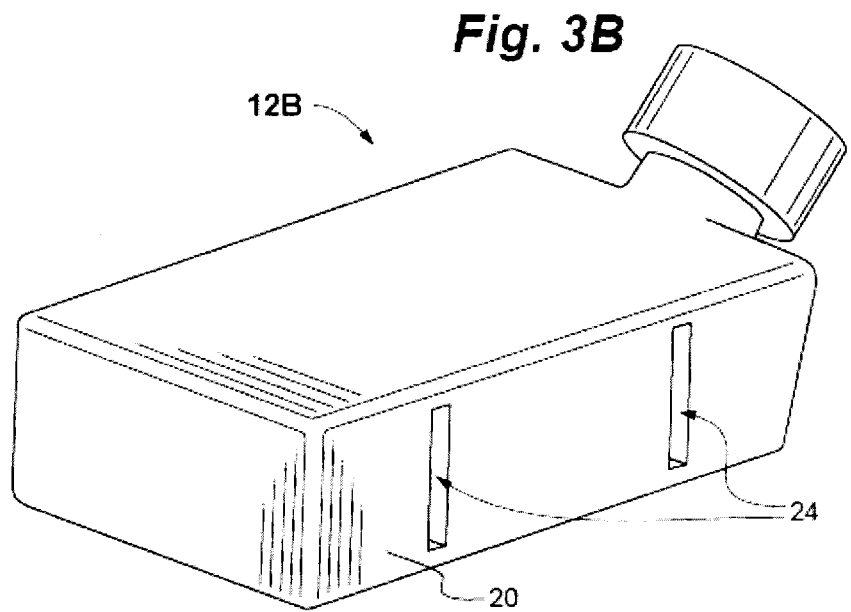
FIG. 3B is a cross-sectional view of an illustrative embodiment of the present invention showing how the gas compartment(s) can traverse the gas permeable cell culture device via a sidewall.

FIG. 3B shows a perspective view of an illustrative embodiment of the present invention. Gas permeable cell culture device 12B includes gas compartments 24. Openings to gas compartment 24 are present upon at least one side wall 20.

Figure 3C:
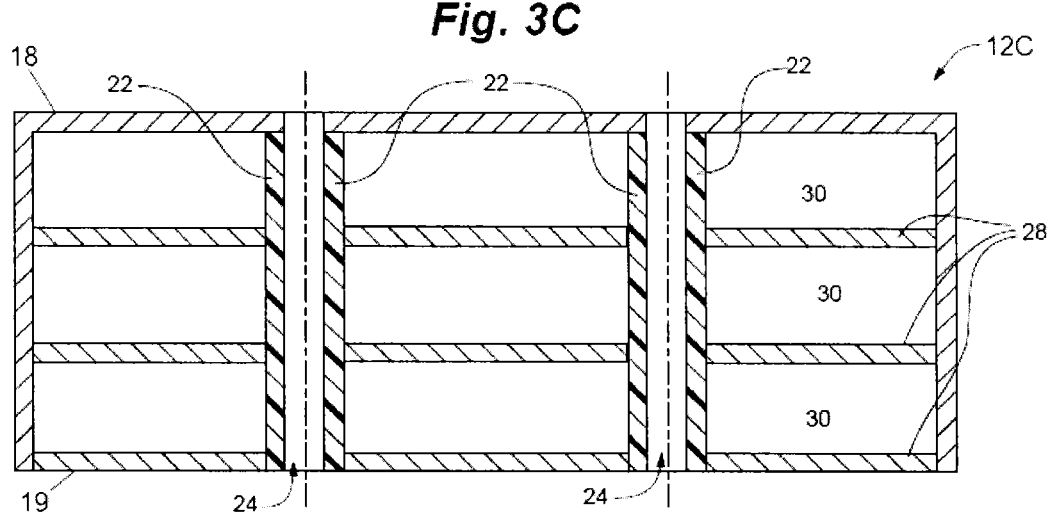
FIG. 3C is a cross-sectional view of an illustrative embodiment of the present invention showing how the gas compartment(s) can move completely through the gas permeable cell culture device.

FIG. 3C shows cross-sectional view of an illustrative embodiment of the present invention. Gas permeable cell culture device 12C includes gas compartments 24 that are structured to create openings that run completely through gas permeable cell culture device 12C. Thus, the openings are present on two opposing walls, in this case top wall 18 and bottom wall 19. Walls 22 of gas compartment 24, comprised of gas permeable material, provide gas transmission to cell compartments 30. Cell compartments 30 are bounded on their lower side by scaffolds 28.

Figure 3D:
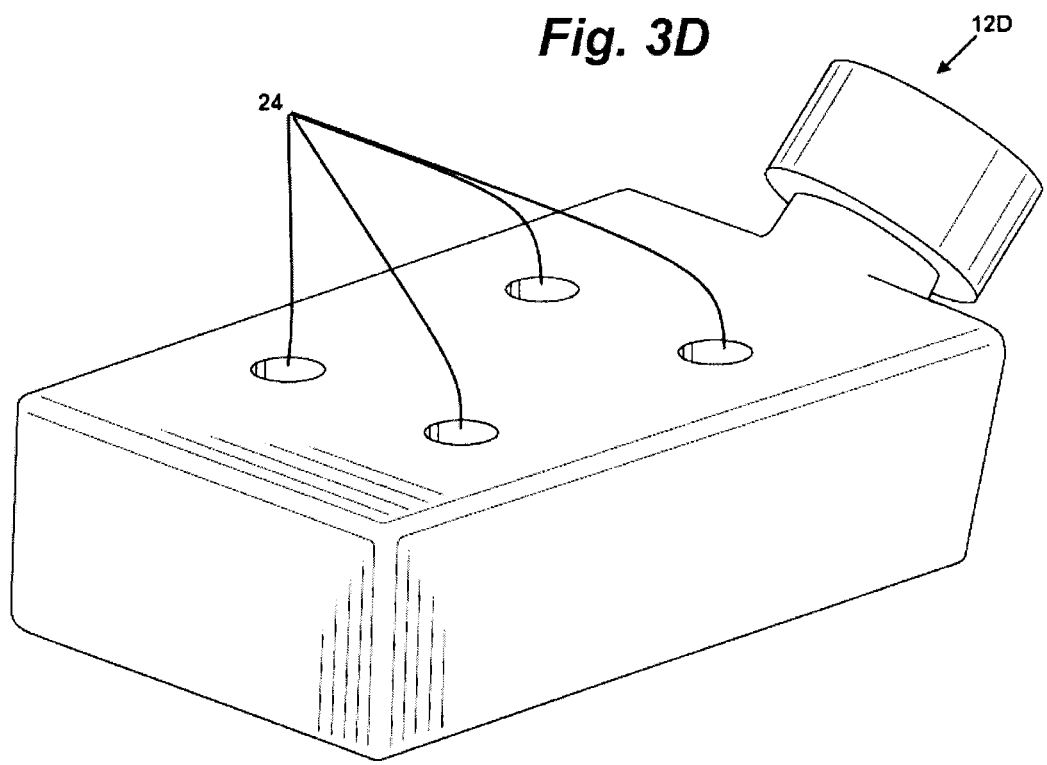
FIG. 3D is a cross-sectional view of an illustrative embodiment of the present invention showing how the gas compartment(s) can have any geometry, in this case a cylindrical compartment with a circular opening.

FIG. 3D shows a perspective view of an illustrative embodiment of the present invention. Gas permeable cell culture device 12D includes circular gas compartments 24 which descend into gas permeable cell culture device 12D.

Gas compartments need not be constrained to the body of the device to be effective. FIG. 4A shows a perspective view of an illustrative embodiment of the present invention. Gas permeable cell culture device 16 includes gas compartments 24 that form a portion of the perimeter walls of gas permeable cell culture device 16. FIG. 4B shows a top view of gas permeable cell culture device 16, showing gas compartments 24. In this configuration, gas compartments 24 act to expand the perimeter of gas permeable device 16 and gas permeable walls 22 act to greatly improve gas transmission into and out of gas permeable device 16. Skilled artisans will recognize that the openings to gas compartment 24 need not be entirely through the top and bottom to greatly increase the surface area for gas transmission. The openings can be through the top and/or bottom and side wall.

Figure 5:
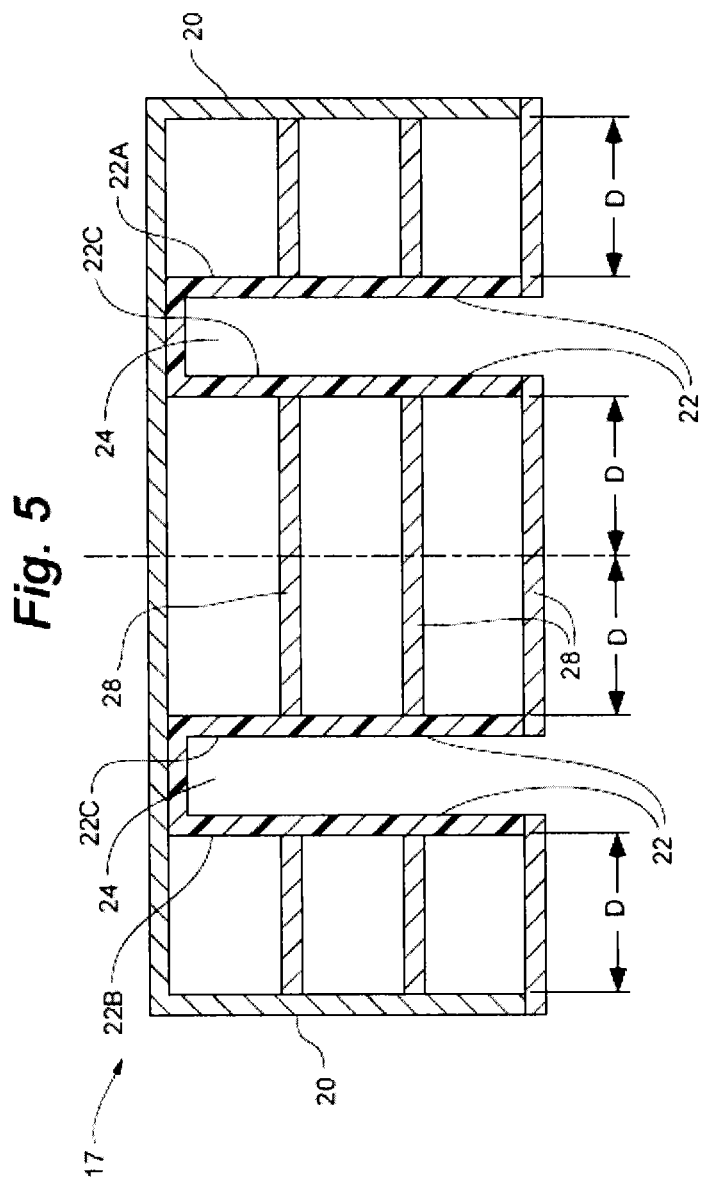
FIG. 5 shows an illustrative embodiment of the present invention with a cross-sectional view showing a preferred method of locating gas compartments in the absence of gas permeable walls at the device perimeter.

Although gas compartments can be any size and shape, it is preferable for the gas compartment structure to be created with the intent of providing the most uniform culture environment in each cell compartment that is possible. The degree to which uniform culture conditions can be established depends upon where the gas compartment(s) are located within the gas permeable culture device. To improve uniformity, a design objective is to create structure that controls the farthest distance that a cell can reside from a gas compartment wall. Preferably, making the gas permeable device a shape that allows gas compartments to be located in a symmetrical pattern relative to the device centerline is one way to provide uniform conditions in the cell culture compartments. FIG. 5 shows an illustrative embodiment of the present invention structured accordingly. It is a cross-sectional view showing a preferred method of locating gas compartments in the absence of gas permeable walls at the device perimeter. In this depiction, two gas compartments 24 ascend into gas permeable cell culture device 17. Scaffolds 28 are uniformly spaced apart and oriented one above the other. To demonstrate that external walls 20 need not be gas permeable for proper function, consider the case where they are not gas permeable in this depiction. Consider gas compartment walls 22 of gas compartments 24 as gas permeable along their entire height and located such that the maximum distance D that a cell can reside from them is fixed throughout the cross-section. In this manner, so long as cells are distributed on the scaffolds uniformly, the oxygen transmission to cells residing at the farthest point D from the gas compartment walls 22 is roughly equivalent throughout the device. The actual distance D can vary depending on the anticipated oxygen demand of the culture. For example, when the gas permeability of walls forming the gas compartments is uniform, the distance D for cultures with high oxygen demand like hepatocytes would be less than for cultures with low oxygen demand like stem cells maintained at low surface density. The gas compartment is preferably structured so that its walls are generally perpendicular to the scaffolds. In that manner, the volume of medium residing in each cell compartment can be generally equal, cell distribution onto scaffolds during inoculum is uniform, and cells residing in each cell compartment are at a similar physical distance from the gas compartment walls. Preferably, designing the gas permeable walls of the gas compartment is done in a manner that provides similar gas transmission capacity to each cell compartment. Thus, when constructing the walls of the gas compartment(s), the area that is gas permeable should be of uniform material type, thickness, and surface area relative to each cell compartment and to every other gas compartment.

Not all walls of the gas compartment need to be gas permeable to create substantially uniform gas transmission across a horizontal cross-section of the gas permeable device. Referring again to FIG. 5, consider the case where walls 20 are gas permeable. If wall 22A and wall 22B of gas compartment 24 are not gas permeable, while walls 22C are gas permeable, a cell residing at any given location on scaffold 28 as viewed in the horizontal cross-section can remain within distance D of a gas transmission location.

Deviating from the preferred relationships between scaffolds and gas compartments is optional, however, when culture demands for gas exchange will not overcome the capacity of the gas compartments to satisfy the gas transmission requirements and when fabrication cost can be reduced by a different structure for the gas compartments. Those skilled in the art will recognize there are many possible configurations that will meet the basic objective of allowing more scalability in the horizontal direction by using gas compartments to improve gas transmission to the cell compartments.

Another consideration for how to physically orient and arrange the gas compartment(s) is the impact the gas compartments can have upon the flow of fluid during medium delivery and removal from the device. Preferably, the gas compartment(s) will be arranged in a manner that facilitates easy fluid flow. The gas compartment(s) should preferably not obstruct medium flow, trap gas in the device, or create highly turbulent flow. The access port location(s) can help overcome these potential undesirable flow characteristics.

Figure 6B:
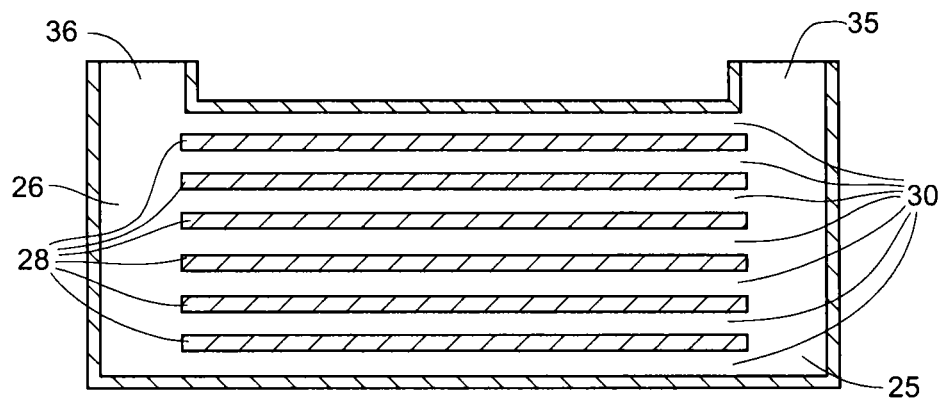
FIG. 6B shows cross section B-B of FIG. 6A revealing an inlet access port and an outlet access port.
Figure 6C:
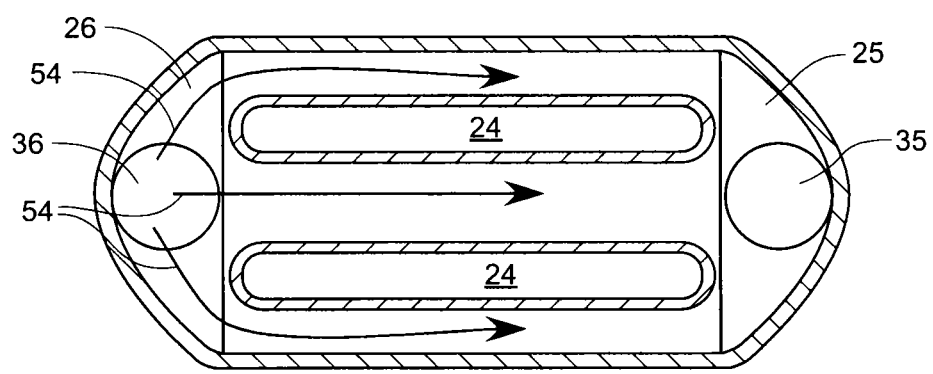
FIG. 6C shows cross-section A-A of FIG. 6A, revealing how fluid can flow from one end of the embodiment to the other.

FIG. 6A, FIG. 6B, and FIG. 6C show an illustrative embodiment of a gas permeable device configured to allow cells and medium to enter the device with minimal turbulence. Cap 37 and cap 38 cover inlet access port 36 and outlet access port 35, which in this depiction are arranged on opposite ends of gas permeable device 18. In this embodiment, the openings to gas compartments 24 are generally rectangular in shape, the longest sides of the openings to gas compartment 24 being oriented in the direction of fluid flow when the medium is added or removed from the device. Stated differently, longest sides of the openings to gas compartment 24 are generally parallel to the device center axis. As with any embodiment, access ports can be structured for closed or open system function. FIG. 6B shows cross-section B-B of FIG. 6A, taken through the device center axis, with access port caps removed. Scaffolds 28 are arranged to form cell compartments 30. Inlet access port 36 and outlet access port 35 communicate with each cell compartment 30 via inlet manifold 26 and outlet manifold 25. In this manner, cell compartments 30 form a conduit from inlet access port 36 to outlet access port 35. FIG. 6C shows cross-section A-A of FIG. 6A, with fluid flow arrows 54 indicating the path that medium and gas take as medium is introduced into inlet access port 36. In this depiction, the shape and location of gas compartments 24 facilitate uniform flow patterns. Those skilled in the art will recognize there are many possible gas compartment configurations and geometric shapes that will meet the basic objective of facilitating uniform fluid flow throughout the gas permeable device. A preferred geometry is a rectangular opening to the gas compartment, the long edge of the rectangular opening being oriented in the direction of, and parallel to, the sidewalls.

Materials used to fabricate the gas permeable devices of this invention can be any of those previously used, or described for use, in cell culture devices and particularly those described in co-pending '814 and '848. Although liquid permeable, gas permeable material can be used as described in co-pending '856, the preferred embodiments utilize liquid impermeable, gas permeable materials. In the preferred embodiment, the device is disposable and materials are optically clear, non cytotoxic, and can be fabricated by injection molding. Various desirable characteristics for scaffolds and gas permeable materials have been previously described in the patents expressly incorporated herein. In addition to the previously described structure for microscopic assessment, gas compartments that descend in the gas permeable device can be structured with an opening that is wide enough to allow a light to shine into the gas compartment in order to facilitate inverted microscopy of the lowest scaffold.

Figure 7B:
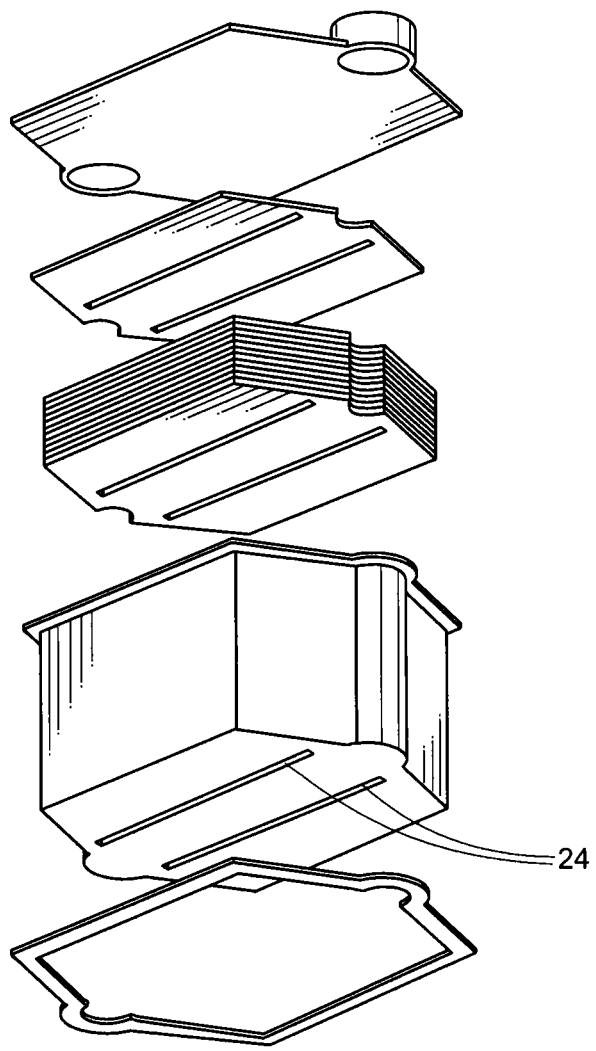
FIG. 7B is another exploded view of the illustrative embodiment shown in FIG. 7A.

In addition to a much more efficient use of space obtained by eliminating the need for a gas-liquid interface above each scaffold while allowing scalability in the horizontal and vertical direction, the ability to easily fabricate the device(s) of this invention allows further cost reduction in the cell culture process. A preferred embodiment integrates traditional flat scaffolds comprised of polystyrene and gas permeable silicone walls is shown in FIG. 7A, FIG. 7B, and FIG. 7C. In the exploded view of FIG. 7A, gas permeable silicone housing 40 resides below a stack of scaffolds 28. In this depiction, each scaffold 28 is separated from its neighboring scaffold 28 by bosses 42, as shown by scaffold 28 that is separated from the stack. A scaffold opening 44 resides in various locations within scaffolds 28 (in this depiction two locations). Scaffold openings 44 are a section of material removed from scaffolds 28 that allows scaffold 28 to fit over gas compartments 24. Preferably, in any embodiment, when discrete sheets of material form scaffolds, sections of material are removed from the scaffolds to allow gas compartments to move through the scaffolds. In this depiction, gas compartments 24 ascend from the bottom of gas permeable silicone housing 40 to move into the void space created by scaffold openings 44 during assembly. Top 46 resides above scaffolds 28. Flange clamp 48 resides below top 46. When scaffolds 28 are placed into gas permeable silicone housing 40, flange clamp 48 is attached to top 46 and a liquid tight seal is formed by squeezing flange 43 of gas permeable silicone housing 40. FIG. 7B shows another view from the bottom of the assembly that reveals the openings to gas compartments 24. If the intent is to culture adherent cells, and the gas permeable device is to be subjected to gamma irradiation, co-pending '856 provides guidance on preparation of the silicone material prior to gamma irradiation so that the surface chemistry of scaffolds is not altered during gamma irradiation.

FIG. 7C shows a cross-sectional view of the assembly shown in FIG. 7A and FIG. 7B, revealing the various components in the assembled state. Flange clamp 48 has secured top 46 and silicone housing 40 in a liquid tight manner by squeezing flange 43. Those skilled in the art of cell culture device design will recognize that there are a wide variety of methods and configurations for creating a liquid tight device. Also, as described previously, the outer walls of the device need not be gas permeable. Thus, the silicone housing need not form the outer walls of the device. In that event, top 46 can be fabricated in a manner that forms the outer walls of the device. Gas compartments 24 have moved through scaffold openings 44 to allow gas compartments 24 to provide gas transmission to culture compartments 30. In the case where the walls of the gas compartments include areas that are silicone, the thickness of the silicone should preferably be less than 0.22 inches, and more preferably 0.01 inches or less to facilitate adequate gas transmission. By ascending into cell culture compartments 30, the orientation of gas compartments 24 facilitate drainage of any condensation that may form when the device is moved back and forth from a standard tissue culture incubator. In general, when selecting the orientation and geometry of the gas compartments, care should be taken to minimize the chance that spills or condensation will collect in areas that could diminish ambient gas contact with the gas permeable areas of the gas compartments. Such an event would alter gas transmission rates into and out of the cell compartments.

Figure 8A:
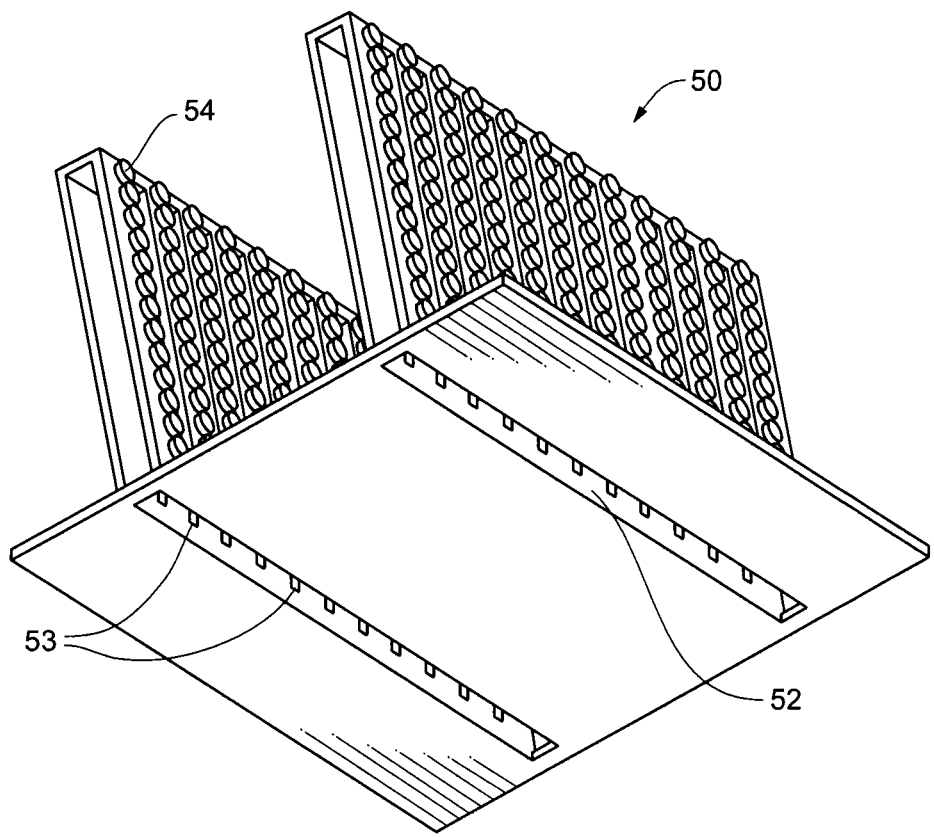
FIG. 8A shows an illustrative embodiment of an optional gas compartment support structure 50.

FIG. 8A shows an illustrative embodiment of an optional gas compartment support structure 50, which acts to serve a similar function as the "gas permeable material support" described in co-pending '814, and/or the "culture compartment support(s)" that are described co-pending '848. In essence, it ensures that gas compartments do not collapse during culture, as may be the case depending on the hydrostatic pressure of the cell culture medium and the structural strength and location of the gas permeable material within the gas compartments. Gas compartment opening 52 allows gas to access the gas compartment. Gas compartment support structure openings 53 allow ambient gas to contact the gas permeable material of the gas compartments. Projections 54 act to keep the walls of the gas compartment at a distance from gas compartment support structure 50 and thereby ensure that gas can move about the surface of the gas permeable portion of the gas compartments.

Figure 8B:
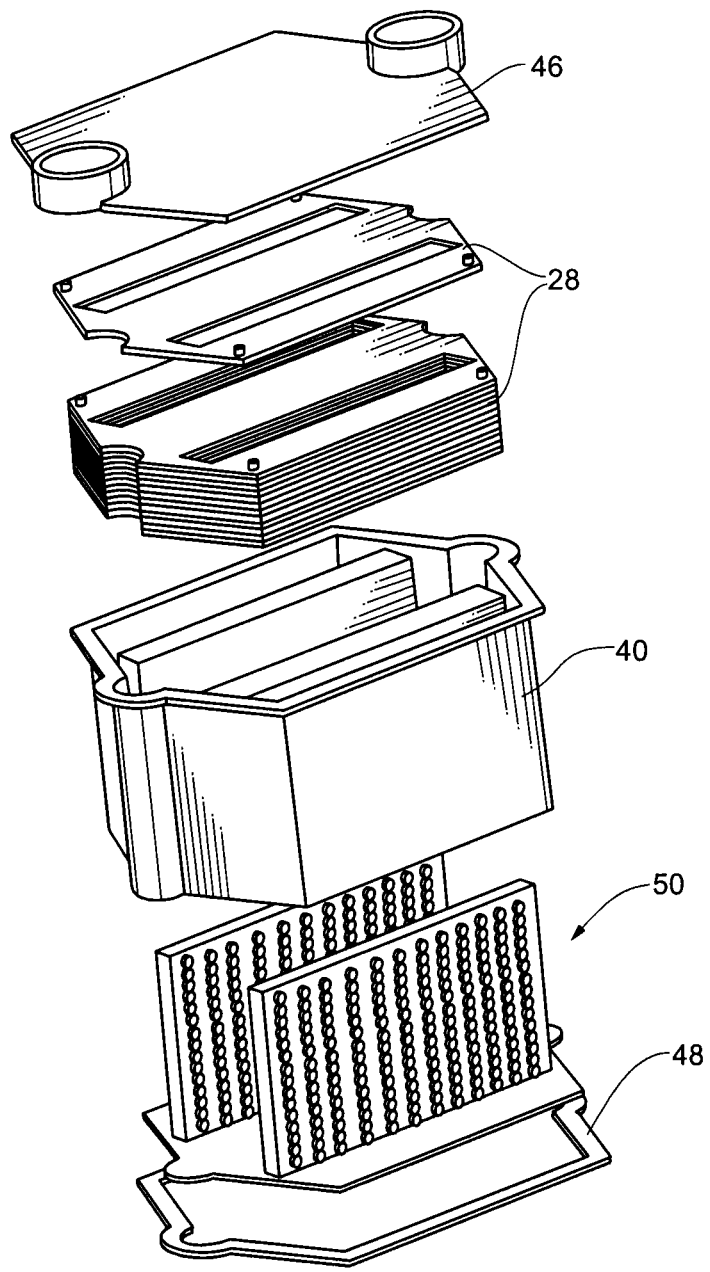
FIG. 8B shows an exploded view of the illustrative embodiment previously described in FIG. 7A with gas compartment support structure 50 in the assembly.
Figure 8C:
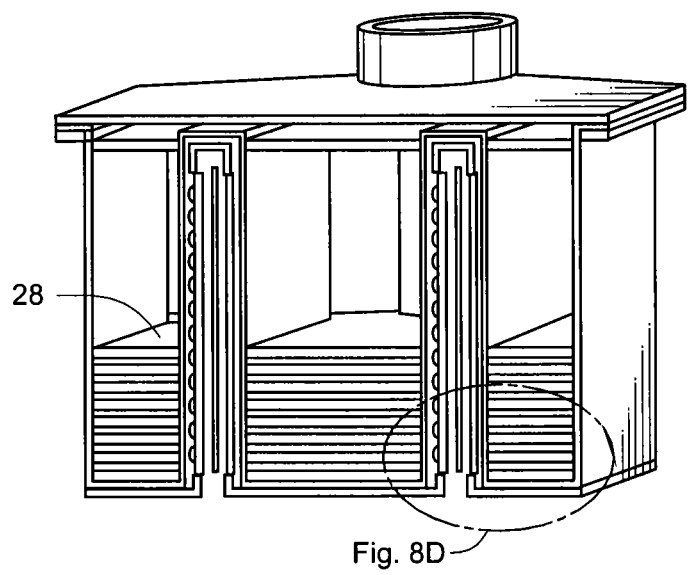
FIG. 8C shows a cross-sectional view of the assembly of FIG. 8B.
Figure 8D:
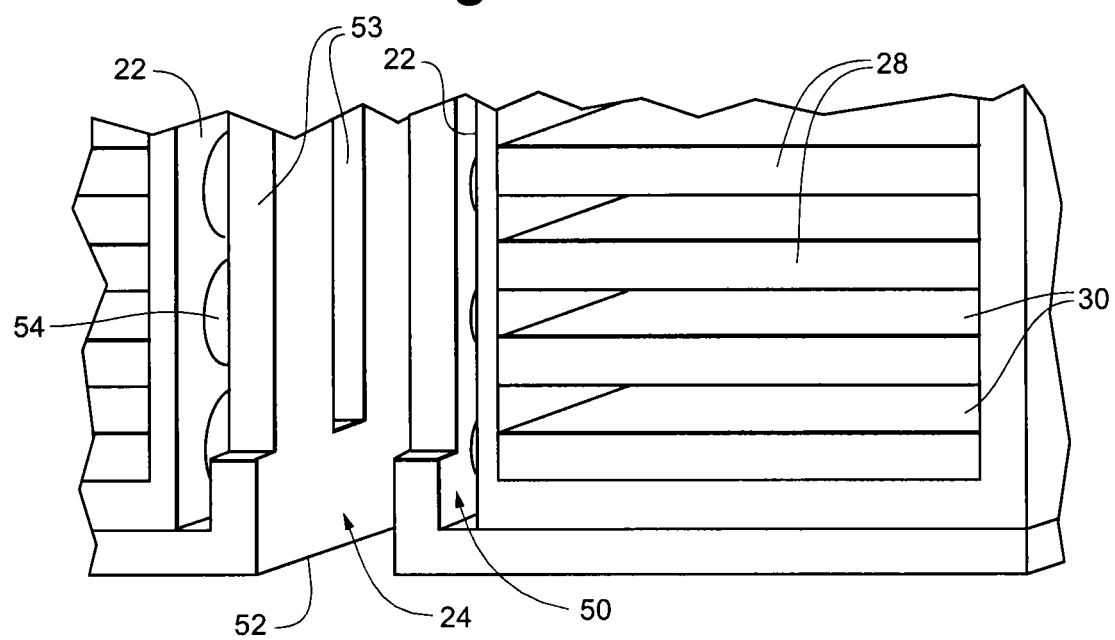
FIG. 8D is a magnified view of the gas compartment support structure of FIG. 8C.

FIG. 8B shows an exploded view of the illustrative embodiment previously described in FIG. 7A with gas compartment support structure 50 in the assembly. FIG. 8C shows a cross-sectional view of the assembly of FIG. 8B. Numerous scaffolds 28 have been removed to simplify the view. Gas compartment support structure 50 is in place, with a magnified view, as illustrated in FIG. 8D, to more clearly show how projections 54 act to contact walls 22 of gas compartment(s) 24, leaving a portion of walls 22 not in contact with gas compartment support structure 50 and thereby allowing walls 22 to be in direct contact with ambient gas. Ambient gas is free to move through gas compartment opening(s) 52 and gas compartment support structure openings 53. Gas transmission to and from cell compartments 30 occurs by way of the wall(s) 22 of gas compartment 24, at least a portion being comprised of gas permeable material.

When structuring any particular configuration of the invention, care should be taken to ensure that the rate of change of $CO_2$ and/or the rate of evaporation are considered. Co-pending '848 can provide guidance as to how to minimize or control undesirable rates of pH change or osmolarity change as a result of an excessive gas transmission rate into and out of the cell compartment.

One preferred method of using the gas permeable device disclosed herein is to form a container that integrates more than one scaffold in a stack, arranged such that the scaffolds reside one atop the other and parallel to neighboring scaffolds with a space between them. The space between each scaffold forms a cell compartment. Each scaffold is preferably a sheet of material, the material being preferably rigid polystyrene. At least one gas compartment resides in the gas permeable device. The gas compartment geometry is such that it has a wall (or walls) that is perpendicular to the scaffolds and is comprised of gas permeable material so that it can provide gas transmission to each cell compartment. The gas permeable device has at least one access port and a manifold that connects the access port to the cell compartments. In use, the access port cap(s) is removed and inoculum is added such that it fills the cell compartments. The access port cap(s) is reattached and acts as a barrier to contamination. The access port(s) can also optionally be structure for closed system fluid introduction and removal. Cells settle to the scaffolds below them. The device is placed in a cell culture incubator where cells are allowed to proliferate. As cells consume oxygen a concentration gradient is formed between the medium in the cell compartment and the ambient gas within the gas compartment. Oxygen moves, by passive convection and diffusion, through the gas permeable material of the gas compartment and into the cell compartment in response. When solutes reach predetermined levels, medium is exchanged.

Figure 9A:
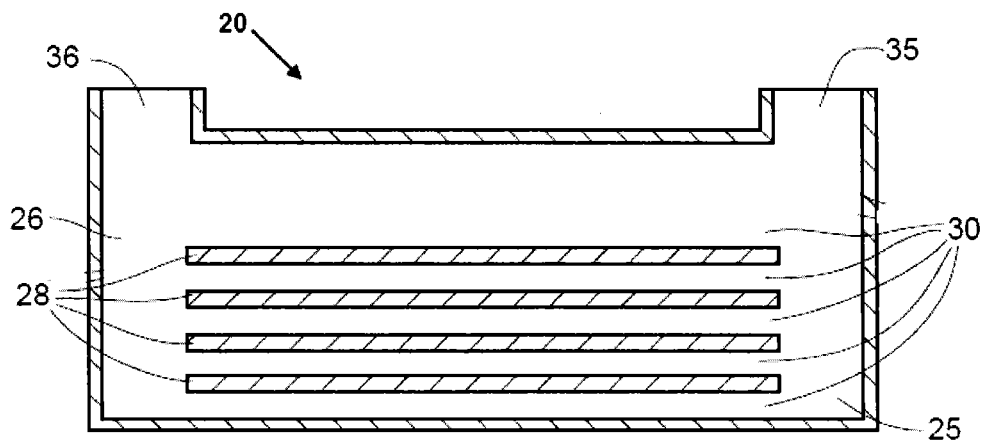
FIG. 9A is a cross-sectional view of an illustrative embodiment of a gas permeable cell culture device that allows the height of medium residing above each scaffold to conform to traditional flasks and multiple shelf flasks but can reduce the feeding frequency relative to traditional flasks.
Figure 9B:
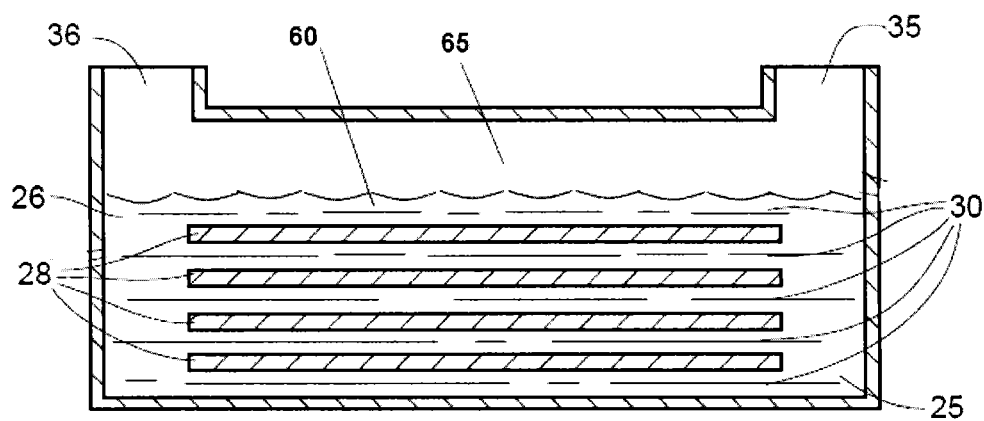
FIG. 9B shows the gas permeable cell culture device of FIG. 9A in use and how medium 60 is added during inoculation such that it resides at a height above the uppermost scaffold 28 that is the same as the height it resides above each other scaffold 28. This allows uniform cell seeding during inoculation.
Figure 9C:
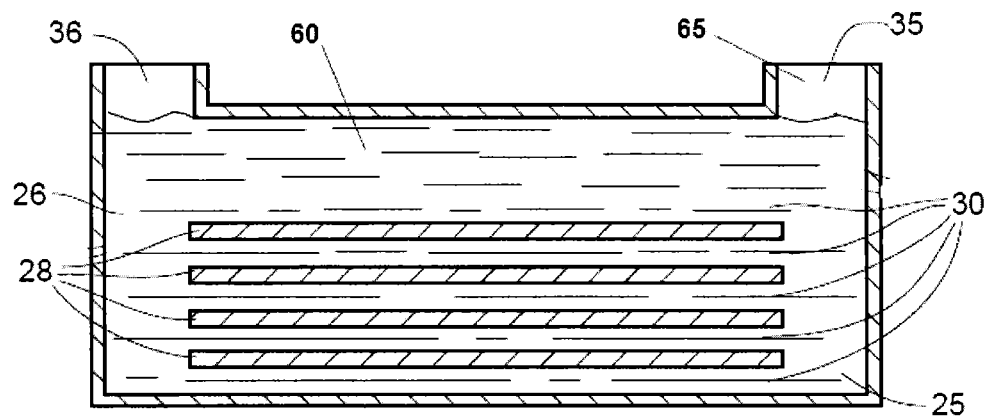
FIG. 9C shows how excess medium 60 can be added to the gas permeable cell culture device of FIG. 9A in order to reduce feeding frequency.

FIG. 9A shows an illustrative embodiment of a gas permeable cell culture device that allows the height of medium residing above each scaffold to conform to traditional flasks and multiple shelf flasks (about 3 mm maximum) but can reduce the feeding frequency relative to traditional flasks. The gas compartment is not shown in the cross-sectional view to help make the depiction more clearly show how the volume of space above the uppermost scaffold 28 can act to decrease feeding frequency. Gas permeable device 20 is structured such that the space above the uppermost scaffold 28 exceeds the space between each scaffold 28, which is preferably equal. As shown in FIG. 9B, when in use, medium 60 is added during inoculation such that it resides at a height above the uppermost scaffold 28 that is the same as the height it resides above each other scaffolds 28. If the goal is to mimic traditional flask conditions, this height is 2 mm to 3 mm. This allows uniform cell seeding to each scaffold 28, including the uppermost scaffold 28, during inoculation. Gas 65 resides above medium 60. Then, after cells are seeded, more medium 60 can be added (herein referred to as "excess medium"), as shown in the cross-sectional view of FIG. 9C. Gas 65 has been displaced by excess medium 60. Solutes in excess medium 60 are capable of moving to each cell compartment 30 by way of manifolds 25 and 26. Also, if scaffolds 28 are not attached in a liquid tight manner to the sides and/or to the gas compartment(s) walls of gas permeable device 20, a gap is created for additional solute movement from excess medium 60 to cell compartments 30. In general, the volume of excess medium will dictate feeding frequency reduction. For example, if the volume of excess medium is equal to the volume of medium that resides below it, feeding frequency can be expected to be reduced by 50%.

Those skilled in the art will recognize that numerous modifications can be made thereof without departing from the spirit of the invention. Therefore, it is not intended to limit the breadth of the invention to the embodiments illustrated and described. Rather, the scope of the invention is to be interpreted by the appended claims and their equivalents.

The invention claimed is:

1. A gas permeable culture device comprising:
   a) an access port, and
   b) a side wall, a top wall, and a bottom wall, and
   c) more than one scaffold oriented one above the other, each of said scaffolds separated by a space, said space forming a cell compartment, and
   d) a manifold that connects said access port to said cell compartments, and
   e) more than one of said scaffolds having at least one scaffold opening and at least one gas compartment residing within a portion of a void space of said scaffold opening of at least more than one of said scaffolds, said gas compartment having an opening in communication with ambient gas and said gas compartment having at least two walls and at least one wall comprised of gas permeable material, and said at least one wall comprised of gas permeable material not being a scaffold, wherein said at least one wall comprised of gas permeable material of said gas compartment is oriented generally perpendicular to said scaffold.

2. The device of claim 1 wherein said one wall of gas permeable material is present in each cell compartment.

3. The device of claim 1 wherein said side wall is comprised of gas permeable material.

4. The device of claim 1 wherein said side wall is not comprised of gas permeable material.

5. The device of claim 1 wherein one opening to said gas compartment is present and is located on said bottom.

6. The device of claim 1 wherein one opening to said gas compartment is present and is located on said top.

7. The device of claim 1 wherein said opening to said gas compartment is located on said side wall.

8. The device of claim 1 wherein said opening to said gas compartment is located on two opposing walls so that said gas compartment is an opening through the entire gas permeable device.

9. The device of claim 1 wherein said opening to said gas compartment is generally rectangular in shape.

10. The device of claim 1 wherein at least a portion of said side wall of the gas permeable device is comprised of gas permeable material.

11. The device of claim 1 wherein said scaffolds include polystyrene material.

12. The device of claim 1 wherein said gas permeable material of said at least one wall of said gas compartment is silicone.

13. The device of claim 12 wherein said silicone is about 0.022 inches or less in thickness.

14. The device of claim 1 wherein opposing ends of the device each include an access port.

15. The device of claim 14 wherein said gas compartment opening is rectangular and the longest sides of said openings to said gas compartment are generally perpendicular to the opposing ends that the access ports reside in proximity of.

16. The device of claim 1 including a gas compartment support structure.

17. The device of claim 1 wherein the space above the uppermost scaffold exceeds the space between any other scaffolds.

18. The device of claim 1 wherein a gap exists between said scaffolds and walls said side wall and/or said one wall of said gas compartment that are adjacent to said scaffolds.

19. The device of claim 1 wherein said opening to said compartment is at least 0.1 inches in width.

20. The device of claim 1 in which the distance of the furthest location on the upper surface of any said scaffold to gas permeable material does not exceed the distance of the furthest location on the upper surface of any other said scaffold to gas permeable material.

21. The device of claim 1 including being full of media.

22. The device of claim 1, wherein at least two walls of said gas compartment are comprised of gas permeable material.

* * * * *